United States Patent [19]

Ienaga et al.

[11] Patent Number: 4,647,574
[45] Date of Patent: Mar. 3, 1987

[54] HYPOGLYCEMIC HYDANTOIN DERIVATIVES

[75] Inventors: Kazuharu Ienaga; Ko Nakamura, both of Yashiro, Japan

[73] Assignee: Nippon Zoki Pharmaceutical Co., Ltd., Osaka, Japan

[21] Appl. No.: 709,861

[22] Filed: Mar. 8, 1985

[30] Foreign Application Priority Data

Mar. 8, 1984 [JP] Japan .................................. 59-45278
Nov. 15, 1984 [JP] Japan ................................ 59-241439

[51] Int. Cl.$^4$ .................... A61K 31/415; C07D 233/72
[52] U.S. Cl. ..................................... 514/390; 514/389; 548/308; 548/311
[58] Field of Search ................ 548/308, 311; 514/389, 514/390

[56] References Cited

U.S. PATENT DOCUMENTS 2,553,055 5/1951 Livak et al. .......................... 548/308
3,395,153 7/1968 Kitasaki et al. ...................... 548/308
3,847,933 11/1974 Tyler .................................... 548/308
4,198,423 4/1980 Rentzea et al. ................. 548/311 X
4,230,709 10/1980 Jamieson ............................. 548/308

FOREIGN PATENT DOCUMENTS 1168914 4/1964 Fed. Rep. of Germany ...... 548/311
45-31959 10/1970 Japan .................................. 548/311
46-35260 10/1971 Japan .................................. 548/311

OTHER PUBLICATIONS

*Chemical Abstracts,* 16:911$^7$ (1922) [Biltz, H., et al., *Berichte,* 54B, 1829-33 (1921)].
*Chemical Abstracts,* 101:23307y (1984) [Tokita, S., et al., *Synthesis,* 1984, (3), 270-1].
*Chemical Abstracts,* 87:183957f (1977) [Ben-Ishai, D., et al., *Tetrahedron,* 1977, 33(10), 1191-6].
*Chemical Abstracts,* 101:181063v (1984) [Jpn. Kokai JP 58,153,934, 9/13/83].
*Chemical Abstracts,* 97:14755q (1982) [Jpn. Kokai JP 81,161,543, 12/11/81].
*Chemical Abstracts,* 96:181198w (1982) [Zanotti, G., et al., *J. Het. Chem.,* 1981, 18(8), 1629-33].
*Chemical Abstracts,* 81:77746c (1974) [Bernardi, L., et al. Ger. Offen. 2,346,535, 4/11/74].
*Chemical Abstracts,* 98:53896b (1983) [Jpn. Kokai JP 57,114,578, 7/16/82].
*Chemical Abstracts,* 91:193262x (1979) [Kolonko, K., et al., *J. Org. Chem.,* 1979, 44(22), 3769-78].
*Chemical Abstracts,* 83:127347n (1975) [Baskakov, Y., et al., *Fiziol. Akt. Veshchestva* 1975, 7, 90-4].

*Primary Examiner*—Richard A. Schwartz
*Attorney, Agent, or Firm*—Pennie & Edmonds

[57] ABSTRACT

The present invention relates to novel hydantoin derivatives represented by the general formula (I) and pharmaceutical compositions containing them as an active ingredient.

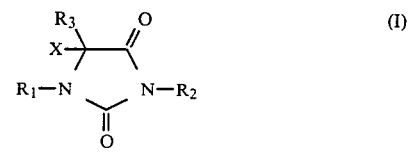

In the formula (I), X is hydrogen or a group having the formula —OR$_4$, and each of R$_1$, R$_2$, R$_3$ and R$_4$, which may be the same or different, is hydrogen, an alkyl group or a cycloalkyl group.

Hydantoin derivatives and pharmaceutically acceptable salts thereof of the present invention have excellent hypoglycemic, hypolipidemic and diuretic effects, as well as low toxicity and great safety. Therefore, the compounds of the present invention are not only useful as antidiabetics but also as drugs for hyperlipidemia.

18 Claims, No Drawings

HYPOGLYCEMIC HYDANTOIN DERIVATIVES

BACKGROUND OF THE INVENTION

The present invention is concerned with novel hydantoin derivatives, pharmaceutically acceptable salts thereof and pharmaceutical compositions containing them as an active ingredient.

Oral sulfonylureas and biguanides having a hypoglycemic effect have been conventionally used for the treatment of diabetes, but they tend to promote certain side effects such as excessive hypoglycemia and lactic acidosis. Insulin, a well-known antidiabetic, can only be administered intravenously due to its chemical nature, and therefore, is troublesome and inconvenient to use.

As a result of investigations for orally administrable hypoglycemic compounds having greater safety than known compounds, the inventors have found hydantoin derivatives and pharmaceutically acceptable salts thereof having excellent hypoglycemic, hypolipidemic and diuretic effects as well as low toxicity and great safety.

An object of the present invention is to provide new, extremely safe, and orally administrable hydantoin derivatives and pharmaceutically acceptable salts thereof having hypoglycemic, hypolipidemic and diuretic effects as well as low toxicity and less side effects than conventional compounds. Another object of the present invention is to provide pharmaceutical compositions containing these hydantoin derivatives and pharmaceutically acceptable salts thereof as an active ingredient.

DETAILED DESCRIPTION OF THE INVENTION

The hydantoin derivatives of the present invention are represented by the following general formula (I):

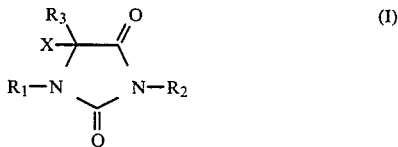

wherein X is hydrogen or a group of the formula —$OR_4$, and each of $R_1$, $R_2$, $R_3$, and $R_4$, which may be the same or different, is hydrogen, an alkyl group, or a cyloalkyl group.

X represents hydrogen or a group having the formula —$OR_4$, in which $R_4$ is hydrogen; an alkyl group, preferably a straight or branched alkyl group having 1 to 20 carbon atoms, such as methyl, ethyl, propyl, iso-propyl, butyl, iso-butyl, sec-butyl, tert-butyl, pentyl, iso-pentyl, neo-pentyl, tert-pentyl, hexyl, iso-hexyl, dimethylbutyl, heptyl, octyl, nonyl, decyl or stearyl; or a cycloalkyl group, preferably having 3 to 8 carbon atoms such as cyclopropyl, cyclobutyl, cyclopentyl, cyclohexyl, cycloheptyl or cyclooctyl. Each of $R_1$, $R_2$ and $R_3$, which may be the same or different, represents hydrogen; an alkyl group, preferably a straight or branched alkyl group having 1 to 20 carbon atoms, such as methyl, ethyl, propyl, iso-propyl, butyl, iso-butyl, sec-butyl, tert-butyl, pentyl, iso-pentyl, neo-pentyl, tert-pentyl, hexyl, iso-hexyl, dimethylbutyl, heptyl, octyl, nonyl, decyl or stearyl; or a cycloalkyl group, preferably having 3 to 8 carbon atoms such as cyclopropyl, cyclobutyl, cyclopentyl, cyclohexyl, cycloheptyl or cyclooctyl.

Preferred compounds of the present invention include:
5-hydroxy-1-methylhydantoin
5-hydroxy-3-methylhydantoin
5-hydroxy-1-ethylhydantoin
5-hydroxy-1-butylhydantoin
5-hydroxy-1-tert-butylhydantoin
5-hydroxy-1-hexylhydantoin
5-hydroxy-1-decylhydantoin
5-hydroxy-1-stearylhydantoin
5-hydroxy-1-cyclopentylhydantoin
5-hydroxy-1-cyclohexylhydantoin
5-hydroxy-1,3-dimethylhydantoin
5-hydroxy-1,5-dimethylhydantoin
5-hydroxy-3,5-dimethylhydantoin
5-hydroxy-1-(1,3-dimethylbutyl)hydantoin
5-hydroxy-1-cyclohexyl-3-methylhydantoin
5-hydroxy-1,3-dicyclohexylhydantoin
5-methoxy-1-methylhydantoin
5-methoxy-3-methylhydantoin
5-ethoxy-1-methylhydantoin
5-buthoxy-3-methylhydantoin
5-methoxy-1-cyclohexylhydantoin
5-methoxy-3-cyclohexylhydantoin
1-methylhydantoin Hydantoin derivatives of the present invention include pharmaceutically acceptable salts of compounds having formula (I) above with alkali metals such as lithium, sodium or potassium, with alkaline earth metals such as calcium or magnesium, with other metals such as aluminum or silver, or with organic bases such as ammonia or organic amines.

These salts may be prepared from free hydantoin derivatives or other salts of these derivatives by known methods.

When optical isomers exist in the compounds of the present invention, the present invention includes any of the dl-, l- and d-isomers.

A. The hydantoin derivatives of the present invention may be prepared by art-recognized methods as indicated herein below.

First, a glyoxylic acid is conventionally esterified. For example, a glyoxylic acid is reacted with an alcohol or 2-methoxyethanol, at room temperature or at a suitable temperature above room temperature or under reflux, for about several hours to about a day, with the produced water being removed, in the presence of an organic acid catalyst such as p-toluenesulfonic acid or camphorsulfonic acid in an aprotic solvent such as benzene, touene, xylene or carbon tetrachloride. Then the produced glyoxylic acid ester or an o-alkylglyoxylic acid ester (glyoxylic acid ester alcoholate) is, without being isolated or further purified, reacted at room temperature or heated under reflux for about 1 hour to about several days with, e.g., N-alkylurea, N-cycloalkylurea, N,N'-dialkylurea or N,N'-dicycloalkylurea in an appropriate solvent such as water, acetic acid or alcohol, such as butanol or mixtures thereof, to give compounds of the present invention represented by the general formula (I).

The above-mentioned reaction can also be carried out with an α-ketocarbonic acid such as pyruvic acid as the starting material instead of a glyoxylic acid.

B. The compounds of the present invention wherein $R_4$ is an alkyl or cycloalkyl group may be produced from a hydantoin derivative as prepared, e.g., by the process described in A, by a conventional O-alkylation process.

The hydantoin derivative is reacted with p-toluenesulfonyl chloride or mesyl chloride to introduce a removable residue into the hydroxy group at the 5-position, in the presence of an organic base such as a lower alkylamine or an alkali metal alkoxide in an appropriate solvent which does not inhibit the reaction. During or after the reaction, the resultant product is reacted with the alcohol corresponding to the $R_4$ of the desired hydantoin derivative to give the compound of the present invention. This O-alkylation may be carried out at room temperature or at a suitable temperature above room temperature or under reflux, for about several hours to about several days.

C. The compounds of the present invention also include products from the N-alkylation of the hydantoin derivatives.

The hydantoin derivative is reacted with a halogenated alkyl, a halogenated cycloalkyl, a dialkylsulfuric acid such as dimethylsulfuric acid, a p-toluenesulfonic acid alkyl ester or a p-toluenesulfonic acid cycloalkyl ester, in the presence of a base such as a lower alkyl amine, an alkali metal alkoxide or a hydroxyalkyl metal in an appropriate solvent which does not inhibit the reaction such as absolute alcohol, or dimethyl sulfoxide. The N-alkylation may be carried out at room temperature or at a suitable temperature above room temperature for about several hours to about several days.

The resultant compounds of the present invention can be purified by known methods such as distillation, chromatography and recrystallization. Identification is established through, inter alia, elemental analysis, melting point, IR, NMR, UV, mass spectrum, etc.

EXAMPLES

The following examples, which are illustrative only and not intended to limit the scope of the invention, describe the preparation of the compounds of the present invention.

EXAMPLE 1

15.0 g of glyoxylic acid n-butyl ester monohydrate and 7.4 g of N-methylurea were refluxed in an 80% aqueous solution of acetic acid for 1 hour. After the solvent was removed by distillation, a small amount of methanol was added to the residue and the insoluble matter was filtered off. The filtrate was then evaporated to dryness under reduced pressure. The resulting crude crystals were recrystallized from ethyl acetate to give 10.4 g of 5-hydroxy-1-methylhydantoin (compound 1) in the form of white crystals.

m.p.: 135.0°–136.0° C.

IR(KBr): 3180, 1750, 1715, 1446, 1115, 750 cm$^{-1}$.

NMR(DMSO-$d_6$) $\delta = 2.72$(s, 3H), 4.98(d, 1H, J=8 Hz), 6.88(d, 1H, J=8 Hz), 10.74(br.s, 1H).

EXAMPLE 2

Using glyoxylic acid as a starting material, 5-hydroxy-3-methylhydantoin (compound 2) was obtained in the same way as in Example 1.

m.p.: 115.5°–116.5° C.

IR(KBr): 3350, 1765, 1700, 1465, 1068, 823 cm$^{-1}$.

NMR(DMSO-$d_6$) $\delta = 2.80$(s, 3H), 5.16(d, 1H, J=8 Hz), 6.72(d, 1H, J=8 Hz), 8.61(s, 1H).

EXAMPLE 3

19.0 g of glyoxylic acid monohydrate were dissolved in a mixture of 80 ml of 2-methoxyethanol and 150-ml of toluene in a 500 ml eggplant type flask fitted up with a Dean-Stark separator. Catalytic amounts of p-toluenesulfonic acid were added to the solution, and it was refluxed overnight. After the reaction mixture was evaporated to dryness under reduced pressure, 18.8 g of N-ethylurea were added to the residue, and 160 ml of acetic acid and 40 ml of water were further added thereto to dissolve them. The mixture was refluxed in an oil bath for 2 hours, and then it was evaporated to dryness, and acetic acid was removed by azeotropic distillation with toluene. The crude product was purified by column chromatography on silica gel (ethyl acetate), and was recrystallized from ethyl acetate to give 23 g of 5-hydroxy-1-ethylhydantoin (compound 3) in the form of white crystals.

m.p.: 119.0°–120.0° C.

IR(KBr): 3340, 1778, 1702, 1470, 1102 cm$^{-1}$.

NMR(DMSO-$d_6$) $\delta = 1.10$(t, 3H, J=7 Hz), 3.14(dq, 1H, $J_1$=14 Hz, $J_2$=7 Hz), 3.34(dq, 1H, $J_1$=14 Hz, $J_2$=7 Hz), 5.09(d, 1H, J=9 Hz), 6.88(d, 1H, J=9 Hz), 10.74(br.s, 1H).

The following compounds were obtained in the same manner:

5-hydroxy-1-butylhydantoin (compound 4)

m.p.: 94.0°–95.0° C.

IR(KBr): 3330, 1778, 1704, 1463, 1080, 750 cm$^{-1}$.

NMR(DMSO-$d_6$) $\delta = 0.89$(t, 3H, J=7 Hz), 1.2–1.4(m, 2H), 1.4–1.6(m, 2H), 3.0–3.4(m, 2H), 5.06(d, 1H, J=8 Hz), 6.88(d, 1H, J=8 Hz), 10.71(br.s, 1H).

5-methoxy-1-methylhydantoin (compound 5)

m.p.: 95.0°–96.0° C.

IR(KBr): 3160, 1764, 1718, 1442, 1080 cm$^{-1}$.

NMR(DMSO-$d_6$) $\delta = 2.79$(s, 3H), 3.21(s, 3H), 5.09(s, 1H), 11.05(br.s, 1H).

5-butoxy-3-methylhydantoin (compound 6)

m.p.: 37.0°–39.0° C.

IR(KBr): 3300, 2950, 1780, 1720, 1462, 1075 cm$^{-1}$.

NMR(DMSO-$d_6$) $\delta = 0.88$(t, 3H, J=7 Hz), 1.2–1.5(m, 2H), 1.4–1.6(m, 2H), 2.83(s, 3H), 3.4–3.6(m, 2H), 5.21(d, 1H, J=2 Hz), 8.84(br.s, 1H).

EXAMPLE 4

5.0 g of 5-hydroxy-1-methylhydantoin (compound 1) were dissolved in absolute methanol and 6.7 g of triethylamine were added to the solution. 10.9 g (1.5 equivalent) of p-toluenesulfonyl chloride were then added to the solution, and was stirred at room temperature for 3 hours. After the reaction mixture was evaporated to dryness, a small amount of water was added to the residue and was extracted with ethyl acetate. The organic layer was dried over sodium sulfate and evaporated to dryness, and the residue was purified by column chromatography on silica gel (ethyl acetate). The obtained crude compound was recrystallized from a mixture of ethyl acetate and hexane to give 3.8 g of 5-methoxy-1-methylhydantoin (compound 5) in the form of white crystals.

The following compounds were obtained in the same manner:

5-ethoxy-1-methylhydantoin (compound 7)

m.p.: 96.0°–97.0° C.

IR(KBr): 3160, 1765, 1720, 1443, 1115 cm$^{-1}$.

NMR(DMSO-$d_6$) $\delta = 1.15$(t, 3H, J=7 Hz), 2.79(s, 3H), 3.43(dq, 1H, $J_1$=2 Hz, $J_2$=7 Hz), 3.56(dq, 1H, $J_1$=2 Hz, $J_2$=7 Hz), 5.08(s, 1H), 11.00(br.s, 1H).

5-methoxy-3-methylhydantoin (compound 8)

m.p.: 57.0°–58.0° C.

IR(KBr): 3300, 1760, 1715, 1468, 1082 cm$^{-1}$.

NMR(DMSO-d$_6$) δ=2.83(s, 3H), 3.26(s, 3H), 5.12(d, 1H, J=2 Hz), 8.85(br.s, 1H).

MS: M$^+$: 144, m/z: 116, 114, 86, 74, 59.

5-methoxy-1-cyclohexylhydantoin (compound 9)

m.p.: 121.0°–122.0° C.

IR(KBr): 3175, 3050, 2940, 2852, 1780, 1700, 1430, 1103, 768 cm$^{-1}$.

NMR(DMSO-d$_6$) δ=0.9–1.35(m, 3H), 1.35–1.7(m, 3H), 1.7–1.9(m, 4H), 3.18(s, 3H), 3.56(tt, 1H, J$_1$=3.6 Hz, J$_2$=12.0 Hz), 5.25 (s, 1H), 11.0(br.s, 1H)

MS: M$^+$: 212, m/z: 197, 182, 169, 131, 103, 98, 82, 67, 60, 55, 41.

EXAMPLE 5

155 g of N-methylurea were added to 214 g of methyl pyruvate in a 3 l eggplant type flask. 800 ml of acetic acid and 200 ml of water were added to dissolve them and the solution was refluxed for 2.5 hours. Then, the reaction mixture was evaporated to dryness and acetic acid was removed by azeotropic distillation with toluene. The obtained crude product was purified by chromatography on silica gel (ethyl acetate and 5% methanol/chloroform) to give 95 g of 5-hydroxy-1,5-dimethylhydantoin (compound 10).

m.p.: 122.0°–123.0° C.

IR(KBr): 3340, 3200, 1780, 1765, 1720, 1440 cm$^{-1}$.

NMR(DMSO-d$_6$) δ=1.34(s, 3H), 2.70(s, 3H), 6.59(s, 1H), 10.78(s, 1H).

MS: M$^+$: 144, m/z: 129, 116, 73, 58, 43.

In the same way, the following compound was obtained.

5-hydroxy-3,5-dimethylhydantoin (compound 11)

m.p.: (oily substance).

NMR(DMSO-d$_6$) δ=1.37(s, 3H), 2.81(s, 3H), 6.50(s, 1H), 8.63(s, 1H).

EXAMPLE 6

21.0 g of glyoxylic acid benzyl ester benzyl alcoholate and 10.0 g of N-hexylurea were refluxed in an 80% aqueous solution of acetic acid for 1.5 hours. After cooling, the reaction mixture was evaporated to dryness under reduced pressure. The obtained crude product was purified by column chromatography on silica gel (ethyl acetate:hexane=1:1) and was recrystallized from benzene to give 1.4 g of 5-hydroxy-1-hexylhydantoin (compound 12) in the form of colorless needle crystals.

m.p.: 96.0°–97.0° C.

IR(KBr): 3360, 3140, 2950, 1780, 1760, 1710, 1475, 1097, 755 cm$^{-1}$.

NMR(DMSO-d$_6$) δ=0.85(t, 3H, J=6.6 Hz), 1.24(s, 6H), 1.3–1.6(m, 2H), 3.09(ddd, 1H, J$_1$=5.9 Hz, J$_2$=8.2 Hz, J$_3$=14.0 Hz), 3.25(ddd, 1H, J$_1$=7.3 Hz, J$_2$=8.2 Hz, J$_3$=14.0 Hz), 5.04(d, 1H, J=8.8 Hz), 6.84(d, 1H, J=8.8 Hz), 10.7(br.s, 1H).

MS: M$^+$: 200, m/z: 129, 116, 89, 85, 58, 41, 30.

The following compounds were obtained in the same manner:

5-hydroxy-1-decylhydantoin (compound 13)

m.p.: 100.0°–101.0° C.

IR(KBr): 3350, 2920, 2855, 1780, 1760, 1710, 1470, 1100, 755 cm$^{-1}$.

NMR(DMSO-d$_6$) δ=0.85(t, 3H, J=6.6 Hz), 1.23(s, 14H), 1.3–1.6(m, 2H), 3.08(ddd, 1H, J$_1$=5.9 Hz, J$_2$=8.1 Hz, J$_3$=13.9 Hz), 3.24(dt, 1H, J$_1$=7.7 Hz, J$_2$=13.9 Hz), 5.03(d, 1H, J=8.8 Hz), 6.84(d, 1H, J=8.8 Hz), 10.7(br.s, 1H).

MS: M$^+$: 256, m/z: 129, 116, 99, 85, 69, 58, 41, 30.

5-hydroxy-1-stearylhydantoin (compound 14)

m.p.: 112.0°–114.0° C.

IR(KBr): 3320, 2910, 2850, 1780, 1760, 1710, 1480, 1095, 750 cm$^{-1}$.

NMR(DMSO-d$_6$) δ=0.84(t, 3H, J=6.6 Hz), 1.23(s, 30H), 1.4–1.6(m, 2H), 3.08(ddd, 1H, J$_1$=6.1 Hz, J$_2$=7.9 Hz, J$_3$=14.0 Hz), 3.24(dd, 1H, J$_1$=6.4 Hz, J$_2$=14.0 Hz), 5.03(d, 1H, J=8.8 Hz), 6.82(d, 1H, J=8.8 Hz), 10.68(br.s, 1H).

MS: M$^+$: 368, m/z: 352, 296, 129, 113, 101, 69, 57, 43, 30.

5-hydroxy-1-cyclopentylhydantoin (compound 15)

m.p.: 139.0°–141.0° C.

IR(KBr): 3320, 2950, 2870, 1778, 1715, 1470, 1078, 763 cm$^{-1}$.

NMR(DMSO-d$_6$) δ=1.3–1.9(m, 8H), 4.00(tt, 1H, J$_1$=8.1 Hz, J$_2$=8.1 Hz), 5.11(d, 1H, J=8.8 Hz), 6.79(d, 1H, J=8.8 Hz), 10.70(br.s, 1H).

MS: M$^+$: 184, m/z: 155, 117, 99, 89, 84, 67, 56, 41, 27.

5-hydroxy-1-cyclohexylhydantoin (compound 16)

m.p.: 176.0°–178.0° C.

IR(KBr): 3310, 2920, 2850, 1770, 1700, 1450, 1115, 753 cm$^{-1}$.

NMR(DMSO-d$_6$) δ=0.9–1.4(m, 3H), 1.4–1.9(m, 7H) 3.51(tt, 1H, J$_1$=4.0 Hz, J$_2$=11.8 Hz), 5.10(d, 1H, J=8.8 Hz), 6.76(d, 1H, J=8.8 Hz), 10.7(br.s, 1H).

MS: M$^+$: 198, m/z: 155, 117, 82, 67, 56, 41, 27.

5-hydroxy-1-(1,3-dimethylbutyl)hydantoin (compound 17)

m.p.: 148.0°–149.0° C.

IR(KBr): 3250, 2950, 1762, 1700, 1445, 1100 cm$^{-1}$.

NMR(DMSO-d$_6$) δ=0.7–1.0(m, 6H), 1.1–1.2(m, 3H), 1.2–1.7(m, 3H), 3.8–4.0(m, 1H), 5.06(d, J=8.8 Hz), [5.10(d, J=8.8 Hz); total 1H], 6.78(d, J=8.8 Hz) [6.80(d, J=8.8 Hz); total 1H], 10.72(br.s, 1H).

MS: M$^+$: 200, m/z: 143, 100, 72, 44, 43, 41.

5-hydroxy-1-tert-butylhydantoin (compound 18)

m.p.: 189.0°–190.5° C.

IR(KBr): 3230, 2965, 1760, 1710, 1436, 1230, 1080 cm$^{-1}$.

NMR(DMSO-d$_6$) δ=1.37(s, 9H), 5.14(s, 1H), 6.78(br.s, 1H), 10.47(br.s, 1H).

MS: M$^+$: 172, m/z: 157, 84, 58, 41

5-hydroxy-1,3-dicyclohexylhydantoin (compound 19)

m.p.: 148.0°–149.0° C.

IR(KBr): 3275, 2930, 2850, 1766, 1700, 1678, 1450, 1112, 760 cm$^{-1}$.

NMR(DMSO-d$_6$) δ=0.9–1.4(m, 6H), 1.4–1.8(m, 12H) 1.8–2.0(m, 2H), 3.54(tt, 1H, J$_1$=4.0 Hz, J$_2$=11.0 Hz), 3.69(tt, 1H, J$_1$=3.8 Hz, J$_2$=12.0 Hz), 5.09(s, 1H), 6.82(br.s, 1H).

MS: M$^+$: 280, m/z: 237, 199, 181, 155, 117, 99, 83, 67, 55, 41.

EXAMPLE 7

750 mg of glyoxylic acid methyl ester methyl alcoholate and 920 mg of N-cyclohexylurea were refluxed in 50 ml of a mixture of acetic acid and methanol (4:1) for 1 hour. After cooling, the solvent was removed by distillation and the residue was purified by column chromatography on silica gel. The obtained crude product was recrystallized from benzene to give 420 mg of 5-methoxy-3-cyclohexylhydantoin (compound 20) in the form of colorless needle crystals.

m.p.: 135.0°–137.0° C.

IR(KBr): 3320, 2915, 2850, 1768, 1710, 1422, 1105 cm$^{-1}$.

NMR(DMSO-d$_6$) δ=0.9-1.4(m, 3H), 1.4-1.8(m, 4H), 1.8-2.1(m, 3H), 3.22(s, 3H), 3.70(tt, 1H, J$_1$=4.0 Hz, J$_2$=14.0 Hz), 5.09(s, 1H), 8.80(br.s, 1H).

MS: M+: 182 m/z: 131, 99, 60, 55, 41

EXAMPLE 8

2.0 g of 5-hydroxy-1-cyclohexylhydantoin were dissolved in 30 ml of methanol containing 600 mg of sodim methoxide. 20 minutes thereafter, 0.7 ml of methyl iodide were added dropwise to the solution and the reaction was continued at 50° C. for 1 hour. The solvent was removed by distillation and the residue was purified by thin layer chromatography on silica gel (ethyl acetate:hexane=1:1). The obtained crude product was recrystallized from benzene to give 500 mg of 5-hydroxy-1-cyclohexyl-3-methylhydantoin (compound 21) in the form of colorless needle crystals.

m.p.: 140.0°-141.0° C.

IR(KBr): 3360, 2940, 2802, 1770, 1700, 1445, 1070, 762 cm$^{-1}$.

NMR(DMSO-d$_6$) δ=0.9-1.4(m, 3H), 1.4-1.9(m, 7H), 2.81(s, 3H), 3.55(tt, 1H, J$_1$=4.0 Hz, J$_2$=11.8 Hz), 5.16(d, 1H, J=8.8 Hz), 6.82(d, 1H, J=8.8 Hz).

MS: M+: 212 m/z: 169, 131, 82, 67, 56, 41, 27

In the same way, the following compound was obtained.

5-hydroxy-1,3-dimethylhydantoin (compound 22)

m.p.: (colorless oily substance).

IR(KBr): 3300, 3000, 1776, 1715, 1195, 703 cm$^{-1}$.

NMR(DMSO-d$_6$) δ=3.02(s, 6H), 5.14(s, 1H), 5.25(br.s, 1H).

MS: M+: 144 m/z: 127, 116, 88, 59, 42.

The following descriptions serve to illustrative pharmaceutical studies of the compounds of the present invention.

(1) Acute toxicity test

The test compounds of the present invention were administered to groups of 10 ddY-strain male mice (weighing about 20 g each), and the LD$_{50}$ values were calculated based on the death rate for 7 days thereafter according to the Litchfield-Wilcoxon's method (Litchfield et al., *J. Pharmacol. Expt. Therap.*, vol. 96, p. 99 (1949)).

None of the mice, which were each administered more than 5,000 mg/kg of the test compounds, either orally, intravenously, intraperitoneally or subcutaneously, died. The mice also had no momentary symptom directly after the administration. Therefore, the LD$_{50}$ values of the compounds of the present invention were more than 5,000 mg/kg. Furthermore, autopsies performed showed no abnormalities in any of the organs after the medication.

(2) Hypoglycemic effect

Groups of 10 Sprague-Dawley-strain male rats (weighing about 250 g each) which had fasted for 18 hours were used for measurement of hypoglycemic effect according to the modified method by Dulin et al. (Dulin et al, *Proc. Soc. Expl. Med.*, 107, 245 (1961)). That is, 0.5 ml/100 g of 20% aqueous solution of glucose was subcutaneously administered into the backs of rats to prevent a decrease in blood glucose level because of the fasting. Immediately thereafter the test drug was orally given, and 2 hours later, the animals underwent laparotomy under pentobarbital anesthesia, then blood was drawn from the inferior vena cava. The obtained blood sample was allowed to stand for 30 minutes to complete the coagulation and was centrifuged to obtain the serum. Blood sugar level was measured according to the mutalotase GOD method (Trinder, *Ann. Clin. Biochem.*, vol. 6, p. 24 (1979)).

Results are tabulated in Table 1.

TABLE 1

| Test Compound | Dosage (mg/kg) | Blood Glucose Level (mg/dl) | Decrease (%) |
|---|---|---|---|
| control | — | 134.6 ± 2.8 | 0 |
| compound 1 | 25 | 89.0 ± 4.1 | 33.9 |
|  | 50 | 87.1 ± 3.3 | 35.3 |
|  | 200 | 81.8 ± 4.0 | 39.2 |
| compound 2 | 200 | 115.5 ± 3.9 | 14.2 |
| compound 3 | 200 | 76.0 ± 3.8 | 43.5 |
| compound 4 | 200 | 82.6 ± 3.6 | 38.6 |
| compound 5 | 200 | 109.4 ± 2.3 | 18.7 |
| compound 15 | 200 | 85.3 ± 5.9 | 36.6 |
| compound 16 | 200 | 89.6 ± 2.7 | 33.4 |
| compound 23 | 200 | 106.9 ± 3.9 | 20.6 |
| Tolubutamide | 50 | 63.4 ± 4.7 | 52.9 |
|  | 100 | 53.0 ± 4.5 | 60.6 |

(compound 23: 1-methylhydantoin)
(control: 0.5% aqueous solution of carboxymethylcellulose (C.M.C.))

(3) Hypolipidemic effect

The test drugs were orally administered to groups of 6 Wisterstrain male rats (each weighing approximately 210-250 g) which had fasted for 20 hours. 2 hours later, the serum was obtained in the same manner as described in (2). Serum triglyceride was measured by GPO-p-chlorophenol colorimetric determination (Richard et al., *Clinical Chemistry*, vol. 24, p. 1343 (1978)) and serum free fatty acid was measured according to the Acyl CoA Synthetase-Acyl CoA Oxidase method (Shimizu, et al., *Biochem. Biophys. Res. Commun.*, vol. 91, p. 108 (1979)).

Results are shown in Table 2.

TABLE 2

| Test Compound | Dosage (mg/kg) | Serum Triglyceride Level (mg/dl) [Decrease (%)] | Serum Fatty Acid Level (mEq/dl) [Decrease (%)] |
|---|---|---|---|
| control | — | 33.5 ± 2.9 [0] | 0.51 ± 0.44 [0] |
| compound 1 | 100 | 10.7 ± 1.3 [68] | 0.17 ± 0.01 [66] |
| compound 2 | 100 | 13.8 ± 0.9 [59] | 0.28 ± 0.04 [45] |
| compound 4 | 100 | 15.3 ± 2.4 [54] | 0.30 ± 0.01 [41] |
| compound 23 | 100 | 18.5 ± 1.8 [45] | 0.29 ± 0.01 [43] |

(control: 0.5% aqueous solution of carboxymethylcellulose (C.M.C.))

(4) Diuretic effect 20 mg/kg of the compound 1 of the present invention were orally administered to Long-Evans strain male rats (weighing about 130-150 g each), and the total amount of excreted sodium within 1 day was then measured according to the method by Lipschitz (*JPFT*, Vol. 79, p. 97 (1943)). The measurements revealed that the amount of excreted sodium on the group of rats which were given compound 1 was 1.8 times as large as on the control group.

Further, in the case of subcutaneous administration to mice, up until 2 hours after the administration, the group which was given compound 1 had a 50.5% increase in the amount of sodium in urine as compared with the control group.

In addition, 200 mg/kg of the compound 1 of the present invention were orally administered to glucose loaded rats and the urine sugar was measured. No difference was found between the medicated and control groups.

As shown by the above-mentioned results, the compounds of the present invention have excellent hypoglycemic effect. The compounds of the present invention are extremely useful as drugs to improve severe hyperglycemia since, even at high doses, they maintain the blood sugar at nearly normal levels. Moreover, the novel compounds have low toxicity and great safety, so that its long-term continuous administration and oral use are possible. Therefore, the compounds are not only useful as antidiabetics, but also as drugs for various diseases caused by diabetes, e.g., diabetic angiopathy, such as diabetic arteriosclerosis, diabetic retinitis, diabetic nephropathy, diabetic neurosis and diabetic microangiopathy. Furthermore, the compounds of the present invention also have a diuretic effect which enhances their utility in treating the aforementioned diseases.

In addition, as shown in Table 2, the compounds of the present invention also have a hypolipidemic effect which makes them useful in treating hyperlipidemia, and in the treatment or the prevention of various diseases caused by hyperlipidemia, such as arteriosclerosis, obesity and cardiopathy.

The compounds of the present invention can be made into pharmaceutical compositions by combining them with appropriate medicinal carriers or diluents, and may be formulated into preparations in solid, semisolid, liquid or gaseous form such as tablets, capsules, powders, granules, ointments, solutions, suppositories, injections, inhalants, aerosols and cataplasms by known methods, for oral or parenteral administration.

In pharmaceutical dosage forms, the compounds of the present invention may be used in the form of their pharmaceutically acceptable salts, and also may be used alone or in appropriate association, as well as in combination with other pharmaceutically active components.

In the case of oral preparations, the compounds may be used alone or combined with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the invention may also be made into ointments by combination with ointment bases such as vaseline, paraffin, plastibase, simple ointment, hydrophilic ointment, hydrophilic vaseline and hydrophilic plastibase.

Furthermore, they may be made into suppositories by mixing with a variety of bases such as emulsifying bases or water-soluble bases.

The compounds of the present invention may be formulated into preparations for injection by dissolving, suspending or emulsifying them in an aqueous or nonaqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the case of inhalations or aerosol preparations, the compounds of the invention in the form of a liquid or minute powder may be placed in an aerosol container with gas or liquid spraying agents, and if desired, with conventional adjuvants such as humidifying agents.

The novel hydantoin derivatives may also be applied as pharmaceuticals as a non-pressurized preparation, such as in a nebulizer or an atomizer.

Cataplasms may be prepared by mixing the compounds with mentha oil, concentrated glycerin, kaolin or other suitable additives.

The desirable dose of the hydantoin derivatives of the present invention varies with the subject, the specific compound, the method and period of administration. However, in order to obtain the desirable effects, it is generally recommended to orally administer 1 to 1000 mg/kg, preferably 5 to 600 mg/kg daily, to an adult. The daily dosage can be administered in several parts, if desired.

In the case of parental administrations, e.g., injections, doses of the compounds on the order of one tenth to one third of the above dosage are preferable as daily doses.

Some prescriptions of the pharmaceutical compositions are shown below as examples which contain the compounds of the present invention as active ingredients. These examples, however, do not limit the instant invention.

| Prescription example 1 (tablet) | |
| --- | --- |
| Component | Content in a tablet (mg) |
| an invented compound | 100 |
| lactose | 130 |
| corn starch | 40 |
| magnesium stearate | 10 |
| Total | 280 mg |

| Prescription example 2 (capsule) | |
| --- | --- |
| Component | Content in a capsule (mg) |
| an invented compound | 50 |
| lactose | 250 |
| Total | 300 mg |

| Prescription example 3 (injection) | |
| --- | --- |
| Component | Content in an ampule (mg) |
| an invented compound | 10 |
| sodium chloride | proper amount |
| distilled water for injection | proper amount |
| Total | 1 ml |

| Prescription example 4 (ointment) | |
| --- | --- |
| Component | Weight (g) |
| an invented compound | 1 |
| emulsified wax | 30 |
| white petrolatum | 50 |
| liquid paraffin | 20 |
| Total | 101 g |

| Prescription example 5 (suppository) | |
|---|---|
| Component | Content in a suppository (mg) |
| an invented compound | 20 |
| cacao butter | 1980 |
| Total | 2000 mg |

What is claimed is:

1. A hydantoin derivative of the formula:

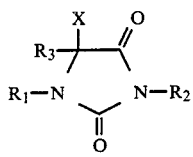

wherein:

X is a group having the formula —OR$_4$; and

R$_1$ is an alkyl group having 4 to 20 carbon atoms or a cycloalkyl group having 3 to 8 carbon atoms, R$_2$ is hydrogen, an alkyl group having 1 to 3 carbon atoms or a cycloalkyl group having 3 to 8 carbon atoms, R$_3$ is hydrogen or an alkyl group having 1 to 3 carbon atoms, and R$_4$ is hydrogen or an alkyl group having 1 to 6 carbon atoms; or pharmaceutically acceptable salt thereof.

2. A hydantoin derivative or pharmaceutically acceptable salt according to claim 1 wherein R$_2$ and R$_3$ each are hydrogen.

3. A hydantoin derivative or pharmaceutically acceptable salt according to claim 2 wherein X has the formula —OR$_4$ and R$_4$ is hydrogen.

4. A hydantoin derivative or pharmaceutically acceptable salt according to claim 3 wherein R$_1$ is an n-butyl group.

5. A hydantoin derivative or pharmaceutically acceptable salt according to claim 3 wherein R$_1$ is a cyclopentyl group.

6. A hydantoin derivative or pharmaceutically acceptable salt according to claim 3 wherein R$_1$ is a cyclohexyl group.

7. A hydantoin derivative according to claim 1, wherein the active ingredient is 5-hydroxy-1-butylhydantoin.

8. A hypoglycemic composition containing a pharmaceutically acceptable carrier and a pharmaceutically effective amount of at least one hydantoin derivative of the formula:

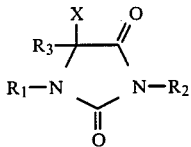

wherein:

X is a group having the formula —OR$_4$; and

R$_1$ is an alkyl group having 4 to 20 carbon atoms or a cycloalkyl group having 3 to 8 carbon atoms, R$_2$ is hydrogen, and alkyl group having 1 to 3 carbon atoms or a cycloalkyl group having 3 to 8 carbon atoms, R$_3$ is hydrogen or an alkyl group having 1 to 3 carbon atoms, and R$_4$ is hydrogen or an alkyl group having 1 to 6 carbon atoms; or pharmaceutically acceptable salt thereof.

9. A hypoglycemic composition comprising an effective amount of 5-hydroxy-1-butylhydantoin and a pharmaceutically acceptable carrier.

10. A hypolipidemic composition containing a pharamceutically acceptable carrier and a pharmaceutically effective amount of at least one hydantoin derivative of the formula:

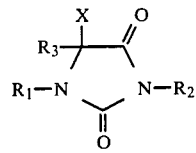

wherein:

X is a group having the formula —OR$_4$; and

R$_1$ is an alkyl group having 4 to 20 carbon atoms or a cycloalkyl group having 3 to 8 carbon atoms, R$_2$ is hydrogen, an alkyl group having 1 to 3 carbon atoms or a cycloalkyl group having 3 to 8 carbon atoms, R$_3$ is hydrogen or an alkyl group having 1 to 3 carbon atoms, and R$_4$ is hydrogen or an alkyl group having 1 to 6 carbon atoms; or pharmaceutically acceptable salt thereof.

11. A hypolipidemic composition comprising an effective amount of 5-hydroxy-1-butylhydantoin and a pharmaceutically acceptable carrier.

12. A diuretic composition containing a pharmaceutically acceptable carrier and a pharmaceutically effective amount of at least one hydantoin derivative of the formula:

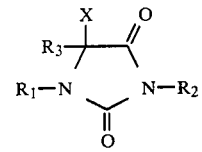

wherein:

X is a group having the formula —OR$_4$; and

R$_1$ is an alkyl group having 4 to 20 carbon atoms or a cycloalkyl group having 3 to 8 carbon atoms, R$_2$ is hydrogen, an alkyl group having 1 to 3 carbon atoms or a cycloalkyl group having 3 to 8 carbon atoms, R$_3$ is hydrogen or an alkyl group having 1 to 3 carbon atoms, and R$_4$ hydrogen or is an alkyl group having 1 to 6 carbon atoms; or pharmaceutically acceptable salt thereof.

13. A method for treating hyperglycemia or hyperlipidemia in mammals which comprises administering an effective amount of at least one hydantoin derivative or pharmaceutically acceptable salt thereof of the formula:

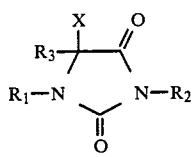

wherein:

X is hydrogen or a group having the formula —OR$_4$; and

R$_1$, R$_2$, R$_3$, and R$_4$, which may be the same or different, each are hydrogen, an alkyl group having 1 to 20 carbon atoms or a cycloalkyl group having 3 to 8 carbon atoms; or pharmaceutically acceptable salt thereof.

14. A method according to claim 13 wherein said compound is 5-hydroxy-1-methylhydantoin.

15. A method according to claim 13 wherein said compound is 5-hydroxy-1-ethylhydantoin.

16. A method according to claim 13 wherein said compound is 5-hydroxy-1-butylhydantoin.

17. A method according to claim 13 wherein said compound is 5-hydroxy-3-methylhydantoin.

18. A method according to claim 13 wherein said compound is 1-methylhydantoin.

* * * * *